United States Patent
Gulsun et al.

(10) Patent No.: US 11,678,853 B2
(45) Date of Patent: Jun. 20, 2023

(54) MULTI-TASK LEARNING FRAMEWORK FOR FULLY AUTOMATED ASSESSMENT OF CORONARY ARTERY DISEASE

(71) Applicant: Siemens Healthcare GmbH, Erlangen (DE)

(72) Inventors: Mehmet Akif Gulsun, Princeton, NJ (US); Diana Ioana Stoian, Brasov (RO); Puneet Sharma, Princeton Junction, NJ (US); Max Schöbinger, Hirschaid (DE); Vivek Singh, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 227 days.

(21) Appl. No.: 17/249,651

(22) Filed: Mar. 9, 2021

(65) Prior Publication Data
US 2022/0287668 A1  Sep. 15, 2022

(51) Int. Cl.
| | | |
|---|---|---|
| *G06T 7/11* | (2017.01) | |
| *A61B 6/00* | (2006.01) | |
| *G06T 11/00* | (2006.01) | |
| *G06N 20/00* | (2019.01) | |
| *G16H 30/20* | (2018.01) | |

(Continued)

(52) U.S. Cl.
CPC ............ *A61B 6/5217* (2013.01); *A61B 6/504* (2013.01); *G06F 18/2431* (2023.01); *G06N 20/00* (2019.01); *G06T 7/0012* (2013.01); *G06T 7/11* (2017.01); *G06T 11/00* (2013.01); *G06V 10/40* (2022.01); *G16H 30/20* (2018.01); *G06T 2207/20081* (2013.01); *G06T 2207/30101* (2013.01)

(58) Field of Classification Search
CPC ......... A61B 6/5217; A61B 6/504; G06T 7/11; G06T 7/0012; G06T 11/00; G06T 2207/20081; G06T 2207/30101; G16H 30/20; G06N 20/00; G06V 10/40; G06K 9/628
See application file for complete search history.

(56) References Cited

U.S. PATENT DOCUMENTS 9,767,557 B1 * 9/2017 Gulsun ............ G06V 30/19173
9,881,372 B2   1/2018 Gulsun et al.
(Continued)

FOREIGN PATENT DOCUMENTS

EP   3786972 A1   3/2021

OTHER PUBLICATIONS

Extended European Search Report (EESR) dated Jul. 6, 2022 in corresponding European Patent Application No. 22161102.3.
(Continued)

*Primary Examiner* — Shefali D Goradia

(57) ABSTRACT

Systems and methods for automated assessment of a vessel are provided. One or more input medical images of a vessel of a patient are received. A plurality of vessel assessment tasks for assessing the vessel is performed using a machine learning based model trained using multi-task learning. The plurality of vessel assessment tasks are performed by the machine learning based model based on shared features extracted from the one or more input medical images. Results of the plurality of vessel assessment tasks or a combination of the results of the plurality of vessel assessment tasks are output.

17 Claims, 10 Drawing Sheets

(51) Int. Cl.
  *G06T 7/00*      (2017.01)
  *G06V 10/40*     (2022.01)
  *G06F 18/2431*   (2023.01)

(56) References Cited

U.S. PATENT DOCUMENTS

| 10,762,637 B2 * | 9/2020 | Gulsun | G06N 3/0445 |
| 11,232,564 B2 * | 1/2022 | Min | G06V 10/761 |
| 2015/0161782 A1 * | 6/2015 | Mohr | G06K 9/00536 |
| | | | 382/128 |

OTHER PUBLICATIONS

Zreik, Majd et al: "A recurrent CNN for Automatic Detection and Classification of Coronary Artery Plaque and Stenosis in Coronary CT Angiography"; Apr. 12, 2018.

Dobko, Mariia et al: "CNN-CASS: CNN for Classification of Coronary Artery Stenosis Score in MPR Images"; Jan. 23, 2020.

Tao Li et al: "Applications of Deep Learning in Fundus Images: A review"; Jan. 25, 2021.

Denzinger, Felix et al: "Automatic CAD-RADS Scoring Using Deep Learning"; Sep. 29, 2020; 16th European Conference; Glasgow, UK; ISSN 0302-9743; pp. 45-54.

Ratner et al., "Data Programming: Creating Large Training Sets, Quickly," 2016, Advances in Neural Information Processing Systems, vol. 29, pp. 3567-3575.

* cited by examiner

Receive one or more input medical images of a vessel of a patient

102

---

Perform a plurality of vessel assessment tasks for assessing the vessel using a machine learning based model trained using multi-task learning, the plurality of vessel assessment tasks performed by the machine learning based model based on shared features extracted from the one or more input medical images

104

---

Output results of the plurality of vessel assessment tasks or a combination of the results of the plurality of vessel assessment tasks

106

US 11,678,853 B2

MULTI-TASK LEARNING FRAMEWORK FOR FULLY AUTOMATED ASSESSMENT OF CORONARY ARTERY DISEASE

TECHNICAL FIELD

The present invention relates generally to fully automated assessment of coronary artery disease, and in particular to a multi-task learning framework for fully automated assessment of coronary artery disease from computed tomography angiography images.

BACKGROUND

CAD (coronary artery disease) is characterized by the reduction of blood flow to the heart due to the build-up of plaque in the arteries of the heart. CAD is the most common type of heart disease. In current clinical practice, coronary CTA (computed tomography angiography) imaging is performed on patients suspected of having CAD for risk stratification and diagnosis.

Conventionally, assessment of CAD from coronary CTA imaging is automatically performed by separately training machine learning based models for performing such medical imaging analysis tasks as, e.g., lesion detection and classification, artifact detection, stenosis grading and lumen segmentation. However, such conventional methods for the automatic assessment of CAD lack consistency between each individual medical imaging analysis task and the overall result. In addition, errors encountered in one medical imaging analysis task may be propagated to downstream medical imaging analysis tasks.

BRIEF SUMMARY OF THE INVENTION

In accordance with one or more embodiments, systems and methods for automated assessment of a vessel are provided. One or more input medical images of a vessel of a patient are received. A plurality of vessel assessment tasks for assessing the vessel is performed using a machine learning based model trained using multi-task learning. The plurality of vessel assessment tasks are performed by the machine learning based model based on shared features extracted from the one or more input medical images. Results of the plurality of vessel assessment tasks or a combination of the results of the plurality of vessel assessment tasks are output.

In one embodiment, the plurality of vessel assessment tasks comprises image-based stenosis grading of a stenosis in the vessel and the image-based stenosis grading of the stenosis in the vessel is performed without using segmentation results of lumen of the vessel.

In one embodiment, the plurality of vessel assessment tasks comprises image-based stenosis grading of a stenosis in the vessel and lumen segmentation from the one or more input medical images, and results of the image-based stenosis grading and results of the lumen segmentation are consistent. In another embodiment, the plurality of vessel assessment tasks comprises a determination of one or more hemodynamic indices and lumen segmentation from the one or more input medical images, and results of the determination of the one or more hemodynamic indices and results of the lumen segmentation are consistent.

In one embodiment, the plurality of medical imaging analysis tasks comprises at least one of detection and classification of disease in the vessel, detection and classification of artifacts in the one or more input medical images, detection and classification of anomalies in the one or more input medical images, image-based stenosis grading of a stenosis in the vessel, and lumen segmentation from the one or more input medical images. The detection and classification of the disease in the vessel may comprise classification of the disease as one of calcified, noncalcified, mixed calcified and noncalcified, and high risk. The detection and classification of the artifacts in the one or more input medical images may comprise classification of artifacts as one of imaging artifacts and image processing artifacts. The detection and classification of the anomalies in the one or more input medical images may comprise classification of anomalies as one of myocardial bridging, and anomalies from prior interventions.

In one embodiment, the machine learning based model is trained using unannotated clinical reports. The results of the plurality of vessel assessment tasks may comprise a heatmap for each of the plurality of vessel assessment tasks.

In one embodiment, a confidence measure for the results of the plurality of vessel assessment tasks or a confidence measure for each of the results of the plurality of vessel assessment tasks are determined.

These and other advantages of the invention will be apparent to those of ordinary skill in the art by reference to the following detailed description and the accompanying drawings.

BRIEF DESCRIPTION OF THE DRAWINGS

FIG. 1 shows a method for automatic assessment of a vessel, in accordance with one or more embodiments;

DETAILED DESCRIPTION

Figure 2:
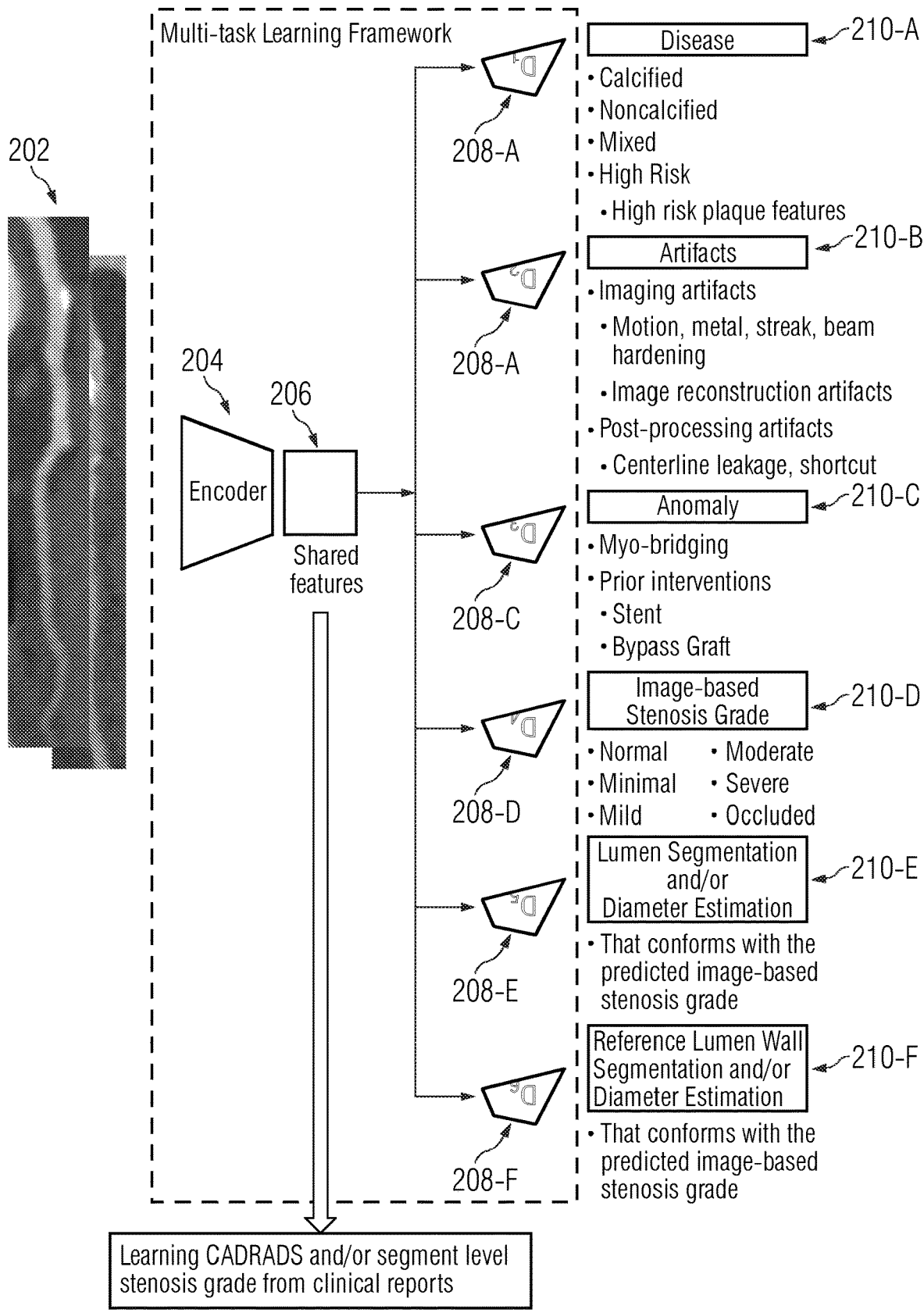
FIG. 2 shows a multi-task learning framework of a machine learning based model trained using multi-task learning to perform a plurality of vessel assessment tasks, in accordance with one or more embodiments.

The present invention generally relates to methods and systems for a multi-task learning framework for fully automated assessment of CAD (coronary artery disease). Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Embodiments described herein are described with reference to the drawings where like reference numerals represent the same or similar elements.

Embodiments described herein provide for a multi-task learning framework for end-to-end training of a single machine learning based model for performing a plurality of medical imaging analysis tasks for the assessment of CAD. By utilizing such a single machine learning based model, results of each of the plurality of medical imaging analysis tasks are ensured to be consistent. In addition, the single end-to-end machine learning based model may produce meaningful results regardless of the failure of an individual medical imaging analysis task.

FIG. 1 shows a method 100 for automatic assessment of a vessel, in accordance with one or more embodiments. The steps of method 100 may be performed by one or more suitable computing devices, such as, e.g., computer 1102 of FIG. 11.

At step 102, one or more input medical images of a vessel of a patient is received. The vessel of the patient may be an artery of the patient, a vein of the patient, or any other vessel of the patient. For example, the vessel may be a coronary branch of the patient. In one embodiment, the input medical images comprise cross-sectional images of the vessel sampled along the vessel. However, the input medical images may comprise any suitable images of the vessel and are not limited to cross-sectional images of the vessel. In some embodiments, the input medical images may include features such as, e.g., reformatted views of the vessel, geometric features of the vessel (e.g., distance to an anatomical landmark or other anatomical object of interest, estimates of the diameter of the vessel, etc.), anatomical features of the vessel (e.g., labels identifying the vessel, indicators of bifurcations in the vessel, etc.), or any other suitable features of the vessel.

In one embodiment, the input medical images are CT (computed tomography) images, such as, e.g., CTA (computed tomography angiography) images. However, the input medical images may be of any other suitable modality, such as, e.g., MRI (magnetic resonance imaging), x-ray, US (ultrasound), or any other modality or combination of modalities. The input medical images may comprise 2D (two dimensional) images or 3D (three dimensional) volumes, and may comprise a single image or a plurality of images (e.g., a sequence of images acquired over time). The input medical images may be received directly from an image acquisition device (e.g., image acquisition device 1114 of FIG. 11), such as, e.g., a CT scanner, as the images are acquired, or can be received by loading previously acquired images from a storage or memory of a computer system or receiving images from a remote computer system.

At step 104, a plurality of vessel assessment tasks for assessing the vessel is performed using a machine learning based model trained using multi-task learning. The plurality of vessel assessment tasks is performed by the machine learning based model based on shared features extracted from the one or more input medical images. The plurality of vessel assessment tasks may be any suitable task for assessing the vessel.

In one embodiment, the plurality of vessel assessment tasks includes detection and classification of a disease (e.g., coronary artery disease), such as, e.g., localization and classification of lesions. The lesions may be classified as being, e.g., calcified, non-calcified, mixed (i.e., calcified and non-calcified), or high-risk. The lesions may be classified as high-risk based on high-risk plaque features such as, e.g., positive remodeling, low attenuation, spotty calcification, and napkin ring sign.

In one embodiment, the plurality of vessel assessment tasks includes detection and classification of artifacts in the input medical images. For example, the detection and classification of artifacts may include localization and classification of imaging artifacts as being, e.g., motion artifacts (e.g., due to cardiac motion, respiratory motion), metal artifacts, streak artifacts, beam hardening artifacts, or image reconstruction artifacts. In another example, detection and classification of artifacts may include the detection of image post-processing artifacts, such as, e.g., centerline leakage or shortcut in traced centerlines.

In one embodiment, the plurality of vessel assessment tasks includes detection and classification of anomalies in the input medical images. For example, the detection and classification of anomalies may include the detection of anatomical anomalies, such as, e.g., myocardial bridging, or anomalies due to prior interventions (e.g., stents, bypass grafts, etc.).

In one embodiment, the plurality of vessel assessment tasks includes image-based stenosis grading of a stenosis in the vessel. As used herein, image-based stenosis grading refers to stenosis grading performed directly from the shared features without using results of a segmentation of the lumen of the vessel. The stenosis may be graded or classified as being, e.g., normal, minimal, mild, moderate, severe, or occluded, or may be graded as percent stenosis.

In one embodiment, the plurality of vessel assessment tasks includes an image-based determination of hemodynamic indices, such as, e.g., FFR (fractional flow reserve), CFR (coronary flow reserve), iFR (instantaneous wave-free ratio), etc., for the vessel. As used herein, image-based determination of hemodynamic indices refers to determination of the hemodynamic indices directly from the shared features without using results of a segmentation of the lumen of the vessel.

In one embodiment, the plurality of vessel assessment tasks includes the generation of geometric models, such as, e.g., lumen segmentation and diameter estimation (e.g., effective diameter or minimum diameter) of the vessel, that conform with the detected features. For example, the lumen of the vessel may be segmented from the input medial images. The segmentation of the lumen of the vessel is consistent with the image-based stenosis grading and the image-based determination of the hemodynamic indices. The segmentation of the lumen of the vessel is consistent with the image-based stenosis grading and the image-based determination of the hemodynamic indices when the image-based stenosis grading and the image-based determination of the hemodynamic indices would be the same or substantially similar to a stenosis grading or a determination of the hemodynamic indices performed based on results of the segmentation of the lumen.

In one embodiment, a confidence measure is also determined for results of the plurality of vessel assessment tasks. The confidence measure may be a confidence measure for the plurality of vessel assessment tasks as a whole, which would indicate a level of consistency between the plurality of vessel assessment tasks. The confidence measure may also be a confidence measure determined for each of the results of the plurality of vessel assessment tasks. The confidence measure may be represented in any suitable form, such as, e.g., a confidence score, a heatmap representing the confidence, etc.

In one embodiment, the machine learning based model comprises 1) an encoder for encoding the one or more input medical images into the shared features (i.e., latent features or a latent representation) and 2) a plurality of decoders each for decoding the shared features to perform a respective one of the plurality of vessel assessment tasks. The machine learning based model is trained to perform the plurality of vessel assessment tasks using multi-task learning during a prior offline or training stage based on annotated training data. In one embodiment, the machine learning based model may be trained in accordance with framework 400 of FIG. 4, described in detail below. Once trained, the trained machine learning based model is applied (e.g., at step 104) to perform the plurality of vessel assessment tasks during an online or testing stage. The machine learning based model may be any suitable machine learning based model or models for performing the plurality of vessel assessment tasks, such as, e.g., a DNN (deep neural network), a CNN (convolutional neural network), a DI2IN (deep image-to-image network), etc.

FIG. 2 shows a multi-task learning framework 200 of a machine learning based model trained using multi-task learning to perform a plurality of vessel assessment tasks, in accordance with one or more embodiments. Framework 200 may be the framework of the machine learning based model applied at step 104 of FIG. 4. In framework 200, encoder 204 of the machine learning based model receives as input one or more input medical images 202 of a vessel of a patient and encodes the one or more input medical images 202 into shared features 206. Decoders D1 208-A, D2 208-B, D3, 208-C, D4 208-D, D5 208-E, and D6 208-F (collectively referred to as a plurality of decoders 208) of the machine learning based model decode shared features 206 to perform a respective vessel assessment task 210-A, 210-B, 210-C, 210-D, 210-E, and 210-F (collectively referred to as a plurality of vessel assessment tasks 210). As shown in framework 200, vessel assessment task 210-A is for detecting and classifying coronary lesions as being calcified, noncalcified, mixed, or high risk (based on high-risk plaque features). Vessel assessment task 210-B is for detecting and classifying artifacts in the one or more input medical images 202 as being imaging artifacts (e.g., motion artifacts, metal artifacts, streak artifacts, beam hardening artifacts, or image reconstruction artifacts) or post-processing artifacts (e.g., centerline leakage or shortcut in traced centerlines). Vessel assessment task 210-C is for detecting and classifying anomalies in the one or more input medical images 202 as being myo-bridging anomalies or anomalies due to prior interventions (e.g., a stent or bypass graft). Vessel assessment task 210-D is for image based stenosis grading as being normal, minimal, mild, moderate, severe, or occluded. Vessel assessment task 210-E is for lumen segmentation and/or diameter estimation from the one or more input medical images 202 that conforms with the results of the image based stenosis grading 210-D. Vessel assessment task 210-F is for reference lumen wall segmentation and/or diameter estimation from the one or more input medical images 202 that conforms with the results of the image based stenosis grading 210-D.

In one embodiment, framework 200 may be trained using clinical reports (e.g., clinician reports, lab diagnostics reports, etc.). In one embodiment, the clinical reports comprise CADRADS (coronary artery disease reporting and data system) reports 212. During the training stage, the machine learning based model may be first pretrained using training medical images and the clinical reports (without annotations) and then fine-tuned based on manual annotations to perform various vessel assessment tasks (e.g., determination of FFR, segmentation based stenosis grading, etc.). Once trained, an encoder 204 of the machine learning based model receives as input clinical reports and encodes the clinical reports into shared features 206. A decoder D5 (not shown in FIG. 2) of the machine learning based model decodes the shared features 206 to perform a vessel assessment task. In one embodiment, the results of the various vessel assessment tasks determined by a machine learning based model trained from clinical reports and results of vessel assessment tasks determined by a machine learning based model trained from manually annotated training data may be combined as multiple evidence for clinical decision making.

At step 106 of FIG. 1, results of the plurality of vessel assessment tasks or a combination of the results of the plurality of vessel assessment tasks are output. For example, the results or the combination of the results of the plurality of vessel assessment tasks can be output by displaying the results or the combination of the results of the plurality of vessel assessment tasks on a display device of a computer system, storing the results or the combination of the results of the plurality of vessel assessment tasks on a memory or storage of a computer system, or by transmitting the results or the combination of the results of the plurality of vessel assessment tasks to a remote computer system. The results or the combination of the results of the plurality of vessel assessment tasks may be input into other systems, such as, e.g., coronary analysis systems.

The results of the plurality of vessel assessment tasks may be in any suitable form. In one embodiment, the results of the plurality of vessel assessment tasks may comprise one or more heatmaps. For example, the results of the plurality of vessel assessment tasks may comprise a heatmap for each of the plurality of vessel assessment tasks, a composite heatmap that incorporates heatmaps for one or more of the plurality of vessel assessment tasks (e.g., in a weighted manner to filter out specific regions), a heatmap of only disease specific results (e.g., stenosis and/or plaque), a heatmap of only non-disease specific results (e.g., motion artifacts), explicit localization of findings of the vessel assessment tasks on the images (i.e., without heatmaps), disease labels on the images (without heatmaps or explicit location of results), transformation of heatmaps into a set of categories (e.g., SCCT (society of cardiovascular computed tomography) grading scale for stenosis severity), etc. An example of a heatmap in shown in FIG. 3.

Figure 3:
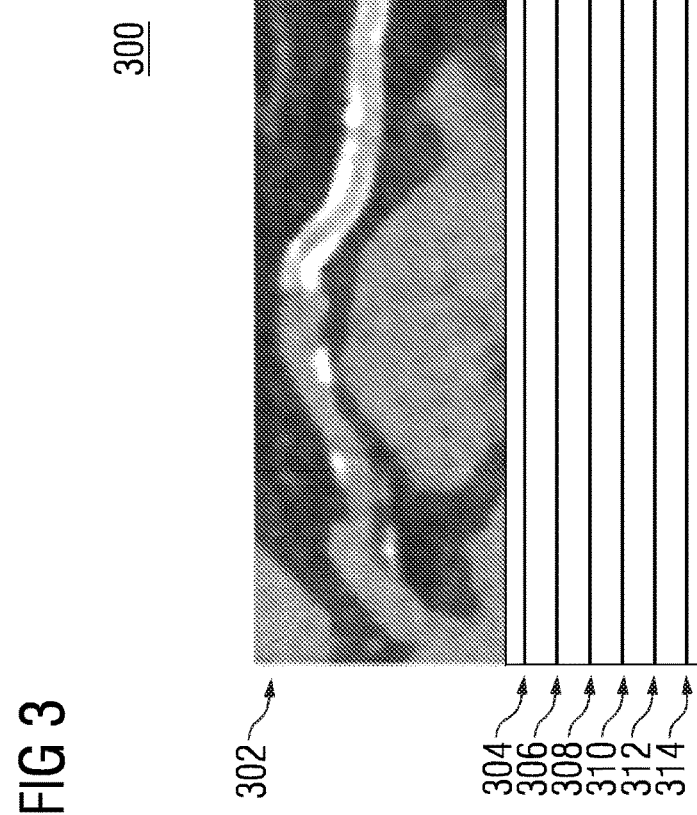
FIG. 3 shows an exemplary composite heatmap for a plurality of vessel assessment tasks, in accordance with one or more embodiments.

FIG. 3 shows an exemplary composite heatmap 300 for a plurality of vessel assessment tasks, in accordance with one or more embodiments. Composite heatmap 300 may be the results of the plurality of vessel assessment tasks output at step 106 of FIG. 1. Composite heatmap 300 shows an input medical image 302 of a vessel and a plurality of corresponding heatmaps 304-314 respectively representing results of a plurality of vessel assessment tasks performed on input medical image 302. As shown in FIG. 3, heatmap 304 shows results of a stenosis grading, heatmap 306 shows results of a classification of lesions as being noncalcified, heatmap 308 shows results of a classification of lesions as being calcified mixed, heatmap 310 shows results of a detection of motion artifacts, heatmap 312 shows results of a detection of anomalies due to a stent, and heatmap 314 shows results of a detection of diseased lesions. Heatmaps 304-314 may be color coded to represent degrees of detection, classification, or other results of the vessel assessment tasks. The horizontal location along the vessel in input medical image 302 corresponds to the horizontal location of heatmaps 304-314.

Advantageously, embodiments described herein enable fully automated assessment of coronary artery disease while producing explainable results of vessel assessment tasks with localization of findings. Embodiments described herein jointly train a single end-to-end machine learning based model for performing a plurality of vessel assessment tasks. This ensures consistency of the results between different vessel assessment tasks, as well as improved performance and generalization by sharing features between related vessel assessment tasks. Embodiments described herein also enable learning from other forms of training data by using the same framework in order to leverage large amounts of clinical reports.

Figure 4:
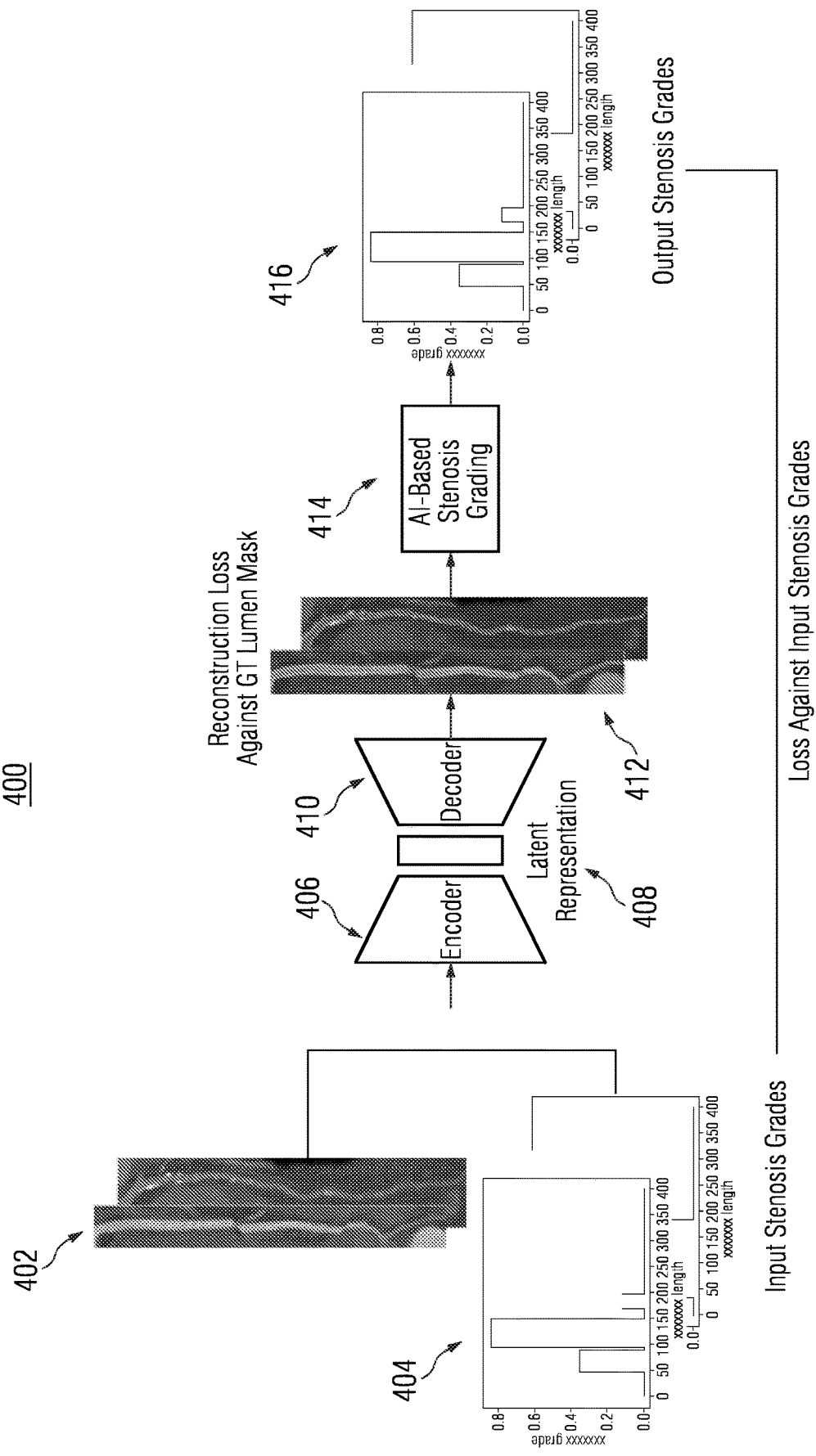
FIG. 4 shows a framework for training machine learning based models for performing a plurality of vessel assessment tasks, in accordance with one or more embodiments.

FIG. 4 shows a framework 400 for training machine learning based models for performing a plurality of vessel assessment tasks, in accordance with one or more embodiments. In one embodiment, framework 400 may be for training the machine learning based model applied at step 104 of FIG. 1. Framework 400 trains the machine learning based model using multi-task learning to perform a plurality of vessel assessment tasks consistent with a lumen segmentation. As shown in framework 400, encoder 406 of a machine learning based model receives as input training medical images 402 of a vessel and corresponding input stenosis grades 404 of a stenosis of the vessel. Encoder 406 encodes training medical images 402 and input stenosis grades 404 into a latent representation 408 (i.e., shared features). Decoder 410 of the machine learning based model decodes latent representation 408 for performing a segmentation of lumen from input training medical images 402 to generate lumen mask 412, as well as for performing other vessel assessment tasks (not shown in framework 400). The machine learning based model is trained with reconstruction loss against ground truth lumen masks. An AI (artificial intelligence) based stenosis grading 414 receives lumen mask 412 as input and determines output stenosis grades 416. Consistency between lumen segmentation 412 and input stenosis grade 404 is ensured by minimizing a loss computed between input stenosis grades 404 and the output stenosis grades 416 predicted based on lumen mask 412.

Figure 5:
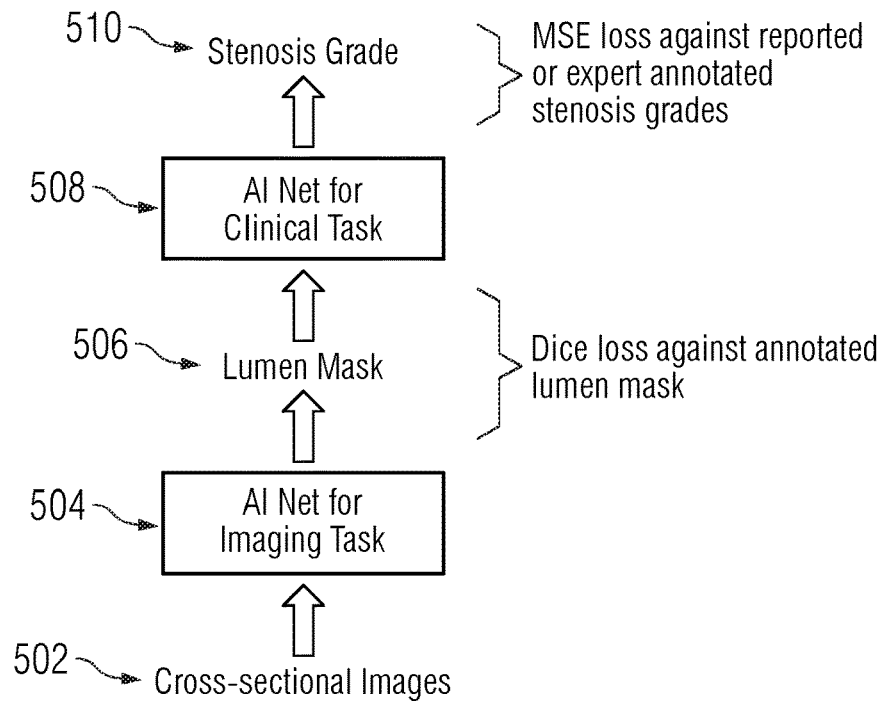
FIG. 5 shows a workflow for training one or more machine learning based models for stenosis grading, in accordance with one or more embodiments.

FIG. 5 shows a workflow 500 for training one or more machine learning based models for stenosis grading, in accordance with one or more embodiments. Workflow 500 may correspond to framework 400 of FIG. 4. For example, AI network 504 for performing an imaging task may be the machine learning based model comprising encoder 406 and decoder 410 in FIG. 4 and AI network 508 for performing a clinical task may perform AI based stenosis grading 414 in FIG. 4. As shown in workflow 500, AI network 504 receives as input one or more cross-sectional images 502 of a vessel and segments lumen from cross-sectional images 502 as lumen mask 506. AI network 508 receives as input lumen mask 506 and generates stenosis grade 510 of the vessel. AI network 504 and AI network 508 are trained in order to optimize a weighted combination of lumen segmentation and stenosis grading. AI network 508 may be trained on synthetically generated lumen masks with known ground truth stenosis grades. The synthetically generated lumen masks may be generated in accordance with FIG. 6. In one embodiment, workflow 500 may be modified to learn the stenosis grading and reference diameter prediction from synthetically generated diameters.

Figure 6:
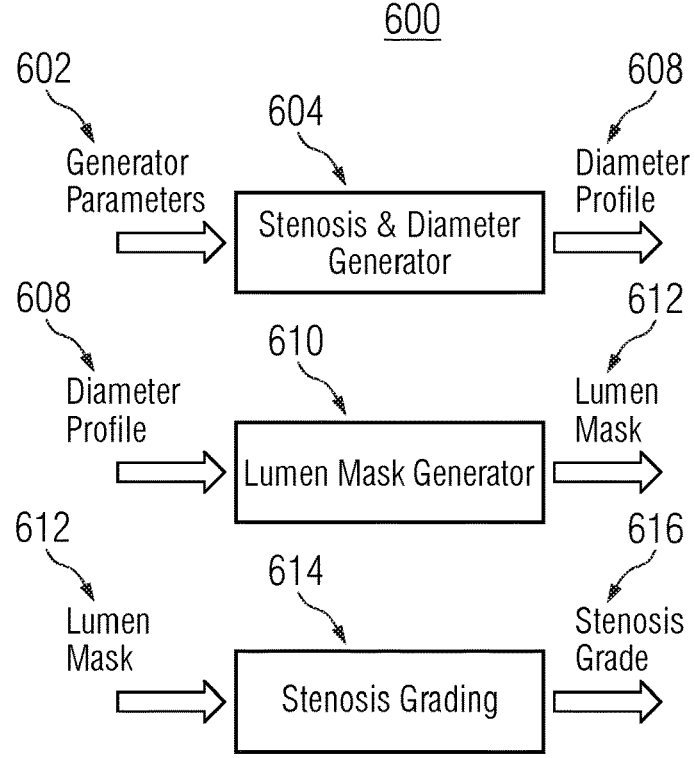
FIG. 6 shows a workflow for generating synthetic data for training one or more machine learning based model for stenosis grading, in accordance with one or more embodiments.

FIG. 6 shows a workflow 600 for generating synthetic data for training one or more machine learning based model for stenosis grading, in accordance with one or more embodiments. Workflow 600 may be performed to generate synthetic data from training AI network 508 of FIG. 5. As shown in workflow 600, stenosis and diameter generator 604 receives as input generator parameters 602 and generates diameter profile 608 of a vessel, lumen mask generator 610 receives as input diameter profile 608 and generates lumen mask 612, and stenosis grading model 614 receives as input lumen mask 612 and generates stenosis grade 616.

Stenosis and diameter generator 604 may be implemented according to a GAN (generative adversarial network) based approach or a rule-based approach to generate diameter profile 608. In the GAN based approach, a generator of the GAN receives as input a latent vector of generator parameters to generate synthetic diameter profiles and a discriminator of the GAN receives the synthetic diameter profiles and real diameter profiles. The discriminator forces the generator to generate realistic synthetic diameter profiles based on the real diameter profiles. In the rule-based approach, a three-step process may be employed to generate diameter profiles 608. In the first step, a skeleton of the vessel geometry is initialized by prescribing the number of branches at each generation of the vessel tree. In the second step, geometric information, such as, e.g., vessel radius, degree of tapering, branch length, bifurcation angle, etc., is prescribed for each generation of the vessel tree. The parameters defining the geometric information may be sampled in pre-specified ranges derived from published literature. In a third step, stenoses are generated in the vessel trees. The number of stenoses on a vessel may be randomly sampled between zero and three for a main branch segment and between zero and two for a side branch segment. The parameters that may be set for each stenosis may include, for example, the maximum degree of radius reduction, the total length, the location of the stenosis center, the length of the stenosis region with minimum radius, and the overall degree of tapering along the stenosis. Stenoses are placed either on a single segment or at a bifurcation. If a bifurcation stenosis is generated, different stenosis parameter values are set for the parent and daughter branches of the bifurcation. Once the stenosis properties are defined, the specific diameters may be generated, e.g., by employing sinusoidal radius variations from max-to-min-to-max diameter values. Additionally, besides the diameter information, non-circularity values may be generated describing, e.g., the degree of cross-sectional flattening. Furthermore, the stenosis grade may be defined directly based on the diameter information, and then corrected or enforced once the lumen mask is generated.

Figure 7:
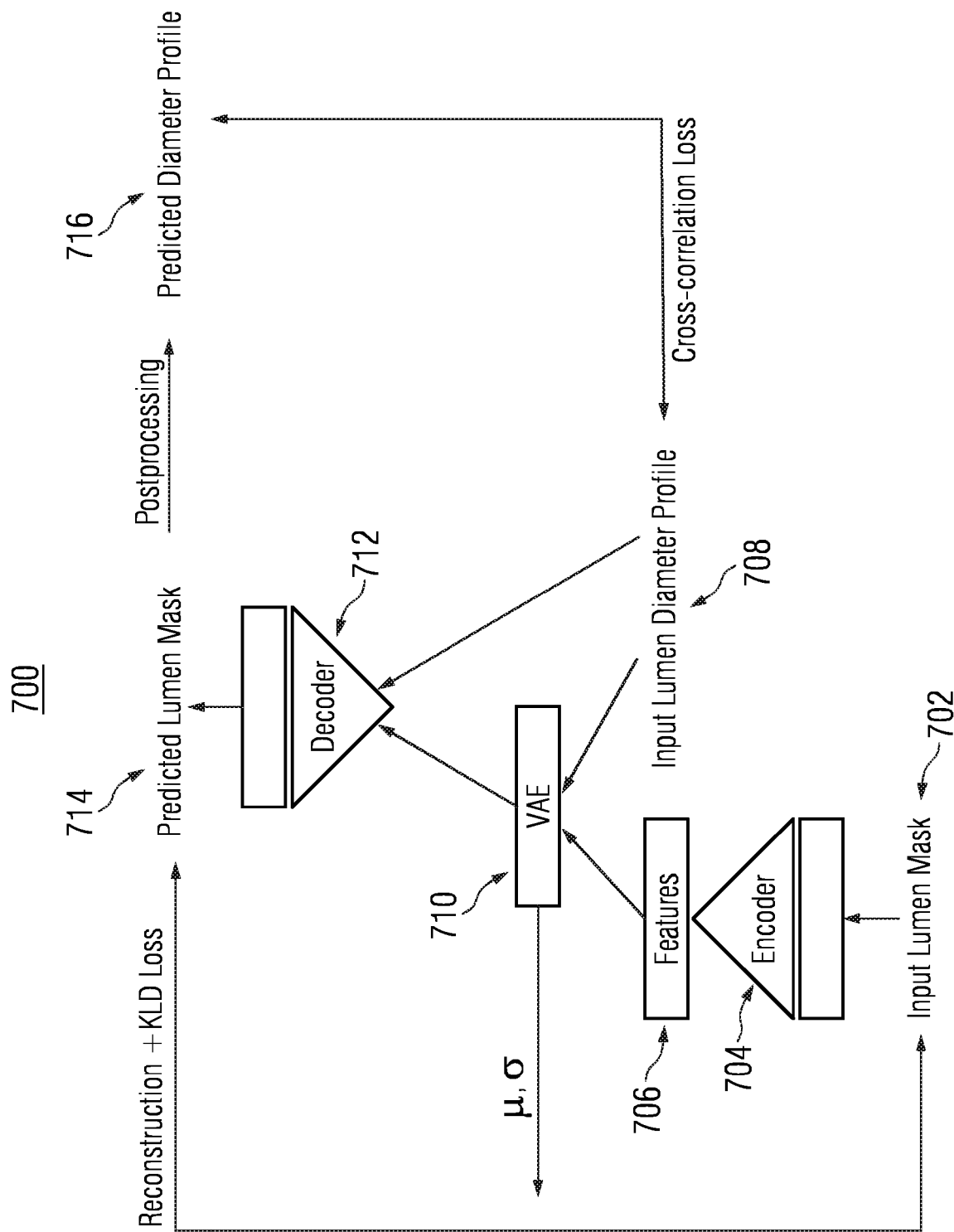
FIG. 7 shows a framework for training a machine learning based model for generating a lumen mask from a diameter profile, in accordance with one or more embodiments.

Lumen mask generator 610 may be implemented based on a VAE (variational autoencoder) network for generating lumen mask 612. FIG. 7 shows a framework 700 for training a machine learning based model for generating a lumen mask from a diameter profile, in accordance with one or more embodiments. In one embodiment, the machine learning based model trained according to framework 700 may be utilized to implement lumen mask generator 610 of FIG. 6. Framework 700 trains the machine learning based network using sequences of lumen masks and their corresponding diameter profiles. In framework 700, encoder 704 receives as input lumen mask 702 and encodes input lumen mask 702 into shared features 706. To add diameter information, input lumen diameter profile 708 is provided as input 1) by concatenating it with features 706 by VAE 710 before sampling from the latent space, and 2) with concatenated features from VAE 710 before decoding. Decoder 712 decodes the concatenated features and input lumen diameter profile 708 to generate predicted lumen mask 714. A predicted diameter profile 716 is then generated from the predicted lumen mask 714 in postprocessing. The predicted diameter profile 716 can be computed using a differentiable function. For example, the area of each lumen mask 714 may be determined and a corresponding equivalent diameter is computed. To validate that the diameter information was considered during reconstruction, the cross-correlation loss is computed between the predicted diameter profile 716 and the input lumen diameter profile 708. The loss of the machine learning based model is comprised from the sum of reconstruction loss, cross-correlation loss, and KLD (Kullback-Leibler divergence) loss.

Figure 8:
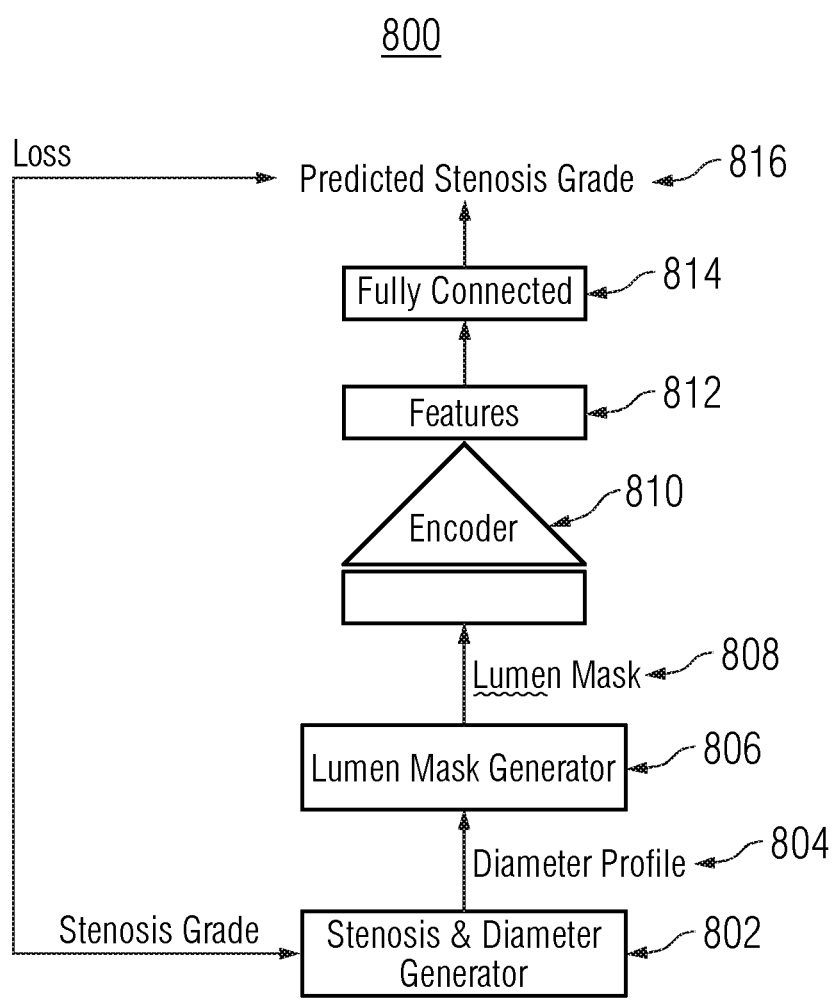
FIG. 8 shows a framework for training a machine learning based network for grading a stenosis, in accordance with one or more embodiments.

Referring to FIG. 6, stenosis grading model 614 may be implemented using a stenosis grading model. FIG. 8 shows a framework 800 for training a machine learning based network for grading a stenosis, in accordance with one or more embodiments. In one embodiment, the machine learning based model trained according to framework 800 may be utilized to implement stenosis grading model 614 of FIG. 6. In framework 800, stenosis and diameter generator 802 generates diameter profile 804 and lumen mask generator 806 generates lumen mask 808 from diameter profile 804. In one embodiment, stenosis and diameter generator 802 may be stenosis and diameter generator 604 of FIG. 6 and lumen mask generator 806 may be lumen mask generator 610 of FIG. 6. The machine learning based network trained according to framework 800 is trained on sequences of synthetic lumen masks, which may be generated in accordance with framework 700 of FIG. 7. Lumen mask 808 is input into encoder 810, which encodes lumen mask 808 into shared features 812. Fully connected network 814 determines a predicted stenosis grade 816 from shared features 812 for each lumen mask 808.

In one embodiment, the machine learning based models utilized to implement stenosis and diameter generator 604, lumen mask generator 610, and stenosis grading 614 of FIG. 6 may be trained in an end-to-end manner using multi-task learning.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 9:
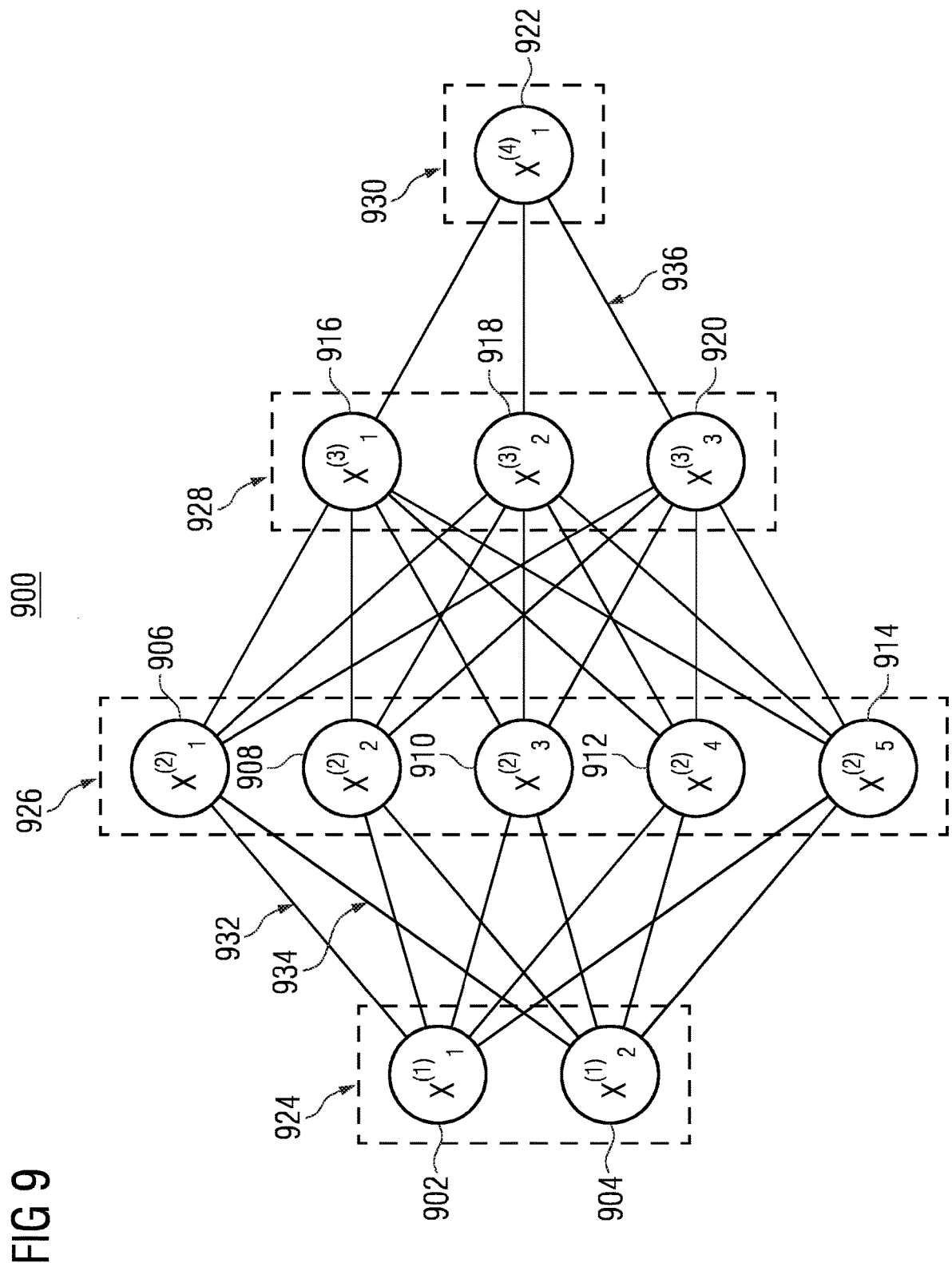
FIG. 9 shows an exemplary artificial neural network that may be used to implement one or more embodiments.

FIG. 9 shows an embodiment of an artificial neural network 900, in accordance with one or more embodiments. Alternative terms for "artificial neural network" are "neural network", "artificial neural net" or "neural net". Machine learning networks described herein may be implemented using artificial neural network 900.

The artificial neural network 900 comprises nodes 902-922 and edges 932, 934, . . . , 936, wherein each edge 932, 934, . . . , 936 is a directed connection from a first node 902-922 to a second node 902-922. In general, the first node 902-922 and the second node 902-922 are different nodes 902-922, it is also possible that the first node 902-922 and the second node 902-922 are identical. For example, in FIG. 9, the edge 932 is a directed connection from the node 902 to the node 906, and the edge 934 is a directed connection from the node 904 to the node 906. An edge 932, 934, . . . , 936 from a first node 902-922 to a second node 902-922 is also denoted as "ingoing edge" for the second node 902-922 and as "outgoing edge" for the first node 902-922.

In this embodiment, the nodes 902-922 of the artificial neural network 900 can be arranged in layers 924-930, wherein the layers can comprise an intrinsic order introduced by the edges 932, 934, . . . , 936 between the nodes 902-922. In particular, edges 932, 934, . . . , 936 can exist only between neighboring layers of nodes. In the embodiment shown in FIG. 9, there is an input layer 924 comprising only nodes 902 and 904 without an incoming edge, an output layer 930 comprising only node 922 without outgoing edges, and hidden layers 926, 928 in-between the input layer 924 and the output layer 930. In general, the number of hidden layers 926, 928 can be chosen arbitrarily. The number of nodes 902 and 904 within the input layer 924 usually relates to the number of input values of the neural network 900, and the number of nodes 922 within the output layer 930 usually relates to the number of output values of the neural network 900.

In particular, a (real) number can be assigned as a value to every node 902-922 of the neural network 900. Here, $x^{(n)}_i$ denotes the value of the i-th node 902-922 of the n-th layer 924-930. The values of the nodes 902-922 of the input layer 924 are equivalent to the input values of the neural network 900, the value of the node 922 of the output layer 930 is equivalent to the output value of the neural network 900. Furthermore, each edge 932, 934, . . . , 936 can comprise a weight being a real number, in particular, the weight is a real number within the interval [−1, 1] or within the interval [0, 1]. Here, $w^{(m,n)}_{i,j}$ denotes the weight of the edge between the i-th node 902-922 of the m-th layer 924-930 and the j-th node 902-922 of the n-th layer 924-930. Furthermore, the abbreviation $w^{(n)}_{i,j}$ is defined for the weight $w^{(n,n+1)}_{i,j}$.

In particular, to calculate the output values of the neural network 900, the input values are propagated through the neural network. In particular, the values of the nodes 902-922 of the (n+1)-th layer 924-930 can be calculated based on the values of the nodes 902-922 of the n-th layer 924-930 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions The transfer function is mainly used for normalization purposes.

In particular, the values are propagated layer-wise through the neural network, wherein values of the input layer 924 are given by the input of the neural network 900, wherein values of the first hidden layer 926 can be calculated based on the values of the input layer 924 of the neural network, wherein values of the second hidden layer 928 can be calculated based in the values of the first hidden layer 926, etc.

In order to set the values $w^{(m,n)}_{i,j}$ for the edges, the neural network 900 has to be trained using training data. In particular, training data comprises training input data and training output data (denoted as $t_i$). For a training step, the neural network 900 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 900 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein $\gamma$ is a learning rate, and the numbers $\delta^{(n)}_j$ can be recursively calculated as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)} = (x_k^{(n+1)} - t_j^{(n+1)}) \cdot f'(\Sigma_i x_i^{(n)} \cdot w_{i,j}^{(n)})$$

if the (n+1)-th layer is the output layer 930, wherein f' is the first derivative of the activation function, and $y^{(n+1)}_j$ is the comparison training value for the j-th node of the output layer 930.

Figure 10:
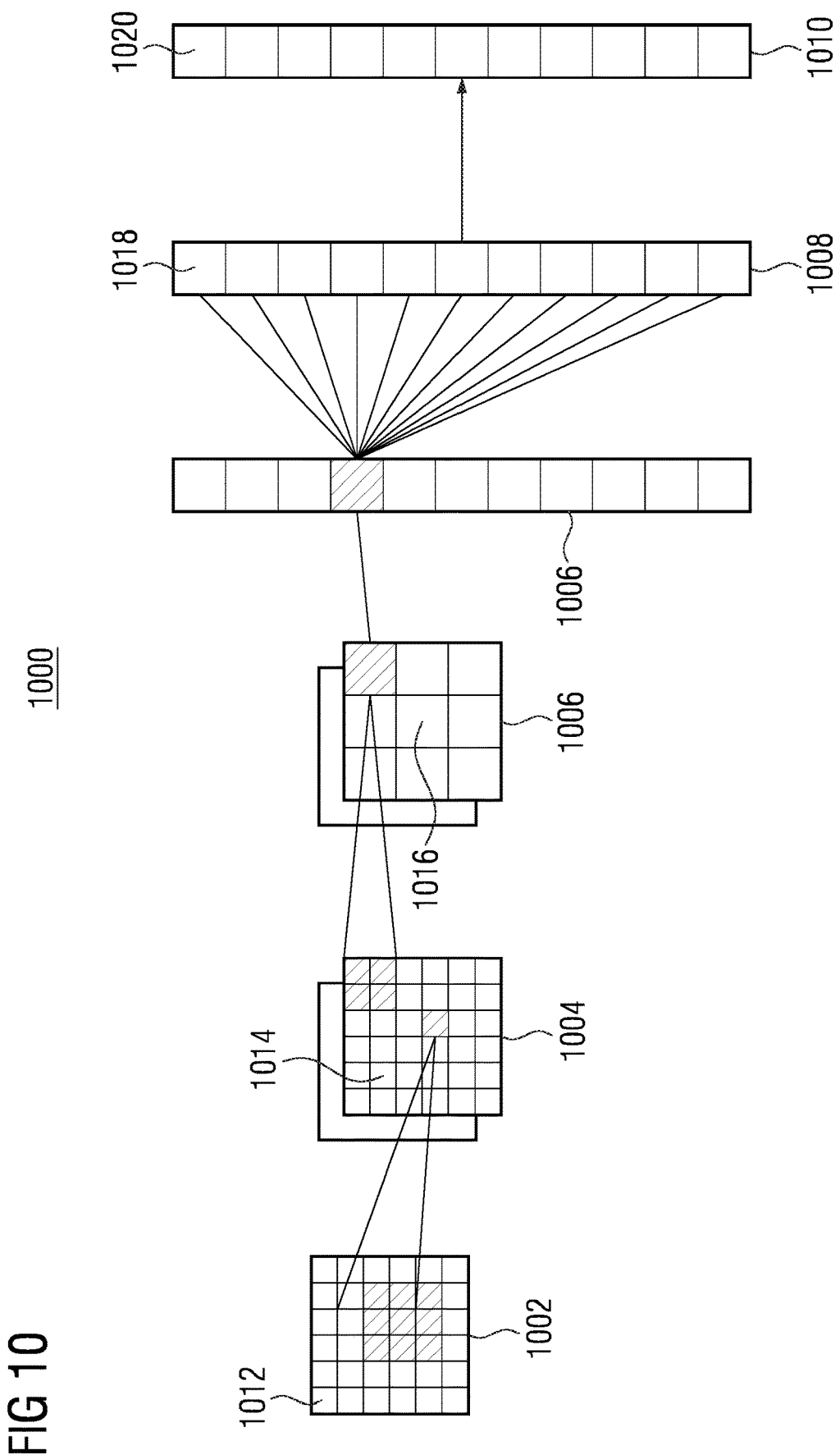
FIG. 10 shows a convolutional neural network that may be used to implement one or more embodiments.

FIG. 10 shows a convolutional neural network 1000, in accordance with one or more embodiments. Machine learning networks described herein may be implemented using convolutional neural network 1000.

In the embodiment shown in FIG. 10, the convolutional neural network comprises 1000 an input layer 1002, a convolutional layer 1004, a pooling layer 1006, a fully connected layer 1008, and an output layer 1010. Alternatively, the convolutional neural network 1000 can comprise several convolutional layers 1004, several pooling layers 1006, and several fully connected layers 1008, as well as other types of layers. The order of the layers can be chosen arbitrarily, usually fully connected layers 1008 are used as the last layers before the output layer 1010.

In particular, within a convolutional neural network 1000, the nodes 1012-1020 of one layer 1002-1010 can be considered to be arranged as a d-dimensional matrix or as a d-dimensional image. In particular, in the two-dimensional case the value of the node 1012-1020 indexed with i and j in the n-th layer 1002-1010 can be denoted as $x^{(n)}_{[i,j]}$. However, the arrangement of the nodes 1012-1020 of one layer 1002-1010 does not have an effect on the calculations executed within the convolutional neural network 1000 as such, since these are given solely by the structure and the weights of the edges.

In particular, a convolutional layer 1004 is characterized by the structure and the weights of the incoming edges forming a convolution operation based on a certain number of kernels. In particular, the structure and the weights of the incoming edges are chosen such that the values $x^{(n)}_k$ of the nodes 1014 of the convolutional layer 1004 are calculated as a convolution $x^{(n)}_k = K_k * x^{(n-1)}$ based on the values $x^{(n-1)}$ of the nodes 1012 of the preceding layer 1002, where the convolution * is defined in the two-dimensional case as $$x_k^{(n)}[i,j] = (K_k * x^{(n-1)})[i,j] = \Sigma_{i'} \Sigma_{j'} K_k[i',j'] \cdot x^{(n-1)}[i-i', j-j'].$$

Here the k-th kernel $K_k$ is a d-dimensional matrix (in this embodiment a two-dimensional matrix), which is usually small compared to the number of nodes 1012-1018 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 1012-1020 in the respective layer 1002-1010. In particular, for a convolutional layer 1004, the number of nodes 1014 in the convolutional layer is equivalent to the number of nodes 1012 in the preceding layer 1002 multiplied with the number of kernels.

If the nodes 1012 of the preceding layer 1002 are arranged as a d-dimensional matrix, using a plurality of kernels can be interpreted as adding a further dimension (denoted as "depth" dimension), so that the nodes 1014 of the convolutional layer 1004 are arranged as a (d+1)-dimensional matrix. If the nodes 1012 of the preceding layer 1002 are already arranged as a (d+1)-dimensional matrix comprising a depth dimension, using a plurality of kernels can be interpreted as expanding along the depth dimension, so that the nodes 1014 of the convolutional layer 1004 are arranged also as a (d+1)-dimensional matrix, wherein the size of the (d+1)-dimensional matrix with respect to the depth dimension is by a factor of the number of kernels larger than in the preceding layer 1002.

The advantage of using convolutional layers 1004 is that spatially local correlation of the input data can exploited by enforcing a local connectivity pattern between nodes of adjacent layers, in particular by each node being connected to only a small region of the nodes of the preceding layer.

In embodiment shown in FIG. 10, the input layer 1002 comprises 36 nodes 1012, arranged as a two-dimensional 6×6 matrix. The convolutional layer 1004 comprises 72 nodes 1014, arranged as two two-dimensional 6×6 matrices, each of the two matrices being the result of a convolution of the values of the input layer with a kernel. Equivalently, the nodes 1014 of the convolutional layer 1004 can be interpreted as arranges as a three-dimensional 6×6×2 matrix, wherein the last dimension is the depth dimension.

A pooling layer 1006 can be characterized by the structure and the weights of the incoming edges and the activation function of its nodes 1016 forming a pooling operation based on a non-linear pooling function f. For example, in the two dimensional case the values $x^{(n)}$ of the nodes 1016 of the pooling layer 1006 can be calculated based on the values $x^{(n-1)}$ of the nodes 1014 of the preceding layer 1004 as $$x^{(n)}[i,j]=f(x^{(n-1)}[id_1,jd_2], \ldots, x^{(n-1)}[id_1+d_1-1,jd_2+d_2-1])$$

In other words, by using a pooling layer 1006, the number of nodes 1014, 1016 can be reduced, by replacing a number $d_1 \cdot d_2$ of neighboring nodes 1014 in the preceding layer 1004 with a single node 1016 being calculated as a function of the values of said number of neighboring nodes in the pooling layer. In particular, the pooling function f can be the max-function, the average or the L2-Norm. In particular, for a pooling layer 1006 the weights of the incoming edges are fixed and are not modified by training.

The advantage of using a pooling layer 1006 is that the number of nodes 1014, 1016 and the number of parameters is reduced. This leads to the amount of computation in the network being reduced and to a control of overfitting.

In the embodiment shown in FIG. 10, the pooling layer 1006 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 1008 can be characterized by the fact that a majority, in particular, all edges between nodes 1016 of the previous layer 1006 and the nodes 1018 of the fully-connected layer 1008 are present, and wherein the weight of each of the edges can be adjusted individually.

In this embodiment, the nodes 1016 of the preceding layer 1006 of the fully-connected layer 1008 are displayed both as two-dimensional matrices, and additionally as non-related nodes (indicated as a line of nodes, wherein the number of nodes was reduced for a better presentability). In this embodiment, the number of nodes 1018 in the fully connected layer 1008 is equal to the number of nodes 1016 in the preceding layer 1006. Alternatively, the number of nodes 1016, 1018 can differ.

Furthermore, in this embodiment, the values of the nodes 1020 of the output layer 1010 are determined by applying the Softmax function onto the values of the nodes 1018 of the preceding layer 1008. By applying the Softmax function, the sum the values of all nodes 1020 of the output layer 1010 is 1, and all values of all nodes 1020 of the output layer are real numbers between 0 and 1.

A convolutional neural network 1000 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 1000 can be trained based on the backpropagation algorithm. For preventing overfitting, methods of regularization can be used, e.g. dropout of nodes 1012-1020, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1. Certain steps or functions of the methods and workflows described herein, including one or more of the steps or functions of FIG. 1, may be performed by a server or by another processor in a network-based cloud-computing system. Certain steps or functions of the methods and workflows described herein, including one or more of the steps of FIG. 1, may be performed by a client computer in a network-based cloud computing system. The steps or functions of the methods and workflows described herein, including one or more of the steps of FIG. 1, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 11:
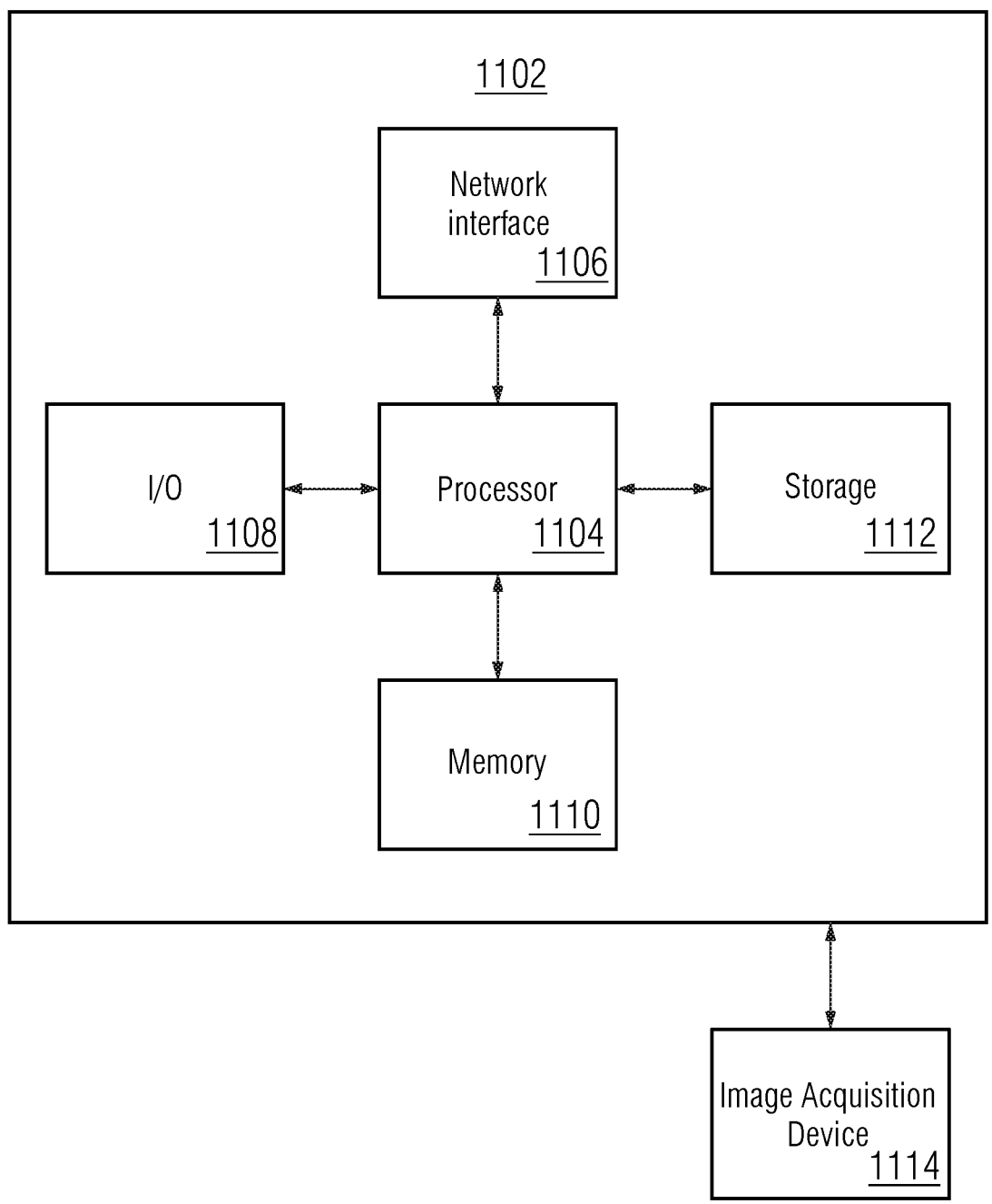
FIG. 11 shows a high-level block diagram of a computer that may be used to implement one or more embodiments.

A high-level block diagram of an example computer 1102 that may be used to implement systems, apparatus, and methods described herein is depicted in FIG. 11. Computer 1102 includes a processor 1104 operatively coupled to a data storage device 1112 and a memory 1110. Processor 1104 controls the overall operation of computer 1102 by executing computer program instructions that define such operations. The computer program instructions may be stored in data storage device 1112, or other computer readable medium, and loaded into memory 1110 when execution of the computer program instructions is desired. Thus, the method and workflow steps or functions of FIG. 2 can be defined by the computer program instructions stored in memory 1110 and/or data storage device 1112 and controlled by processor 1104 executing the computer program instructions. For example, the computer program instructions can be implemented as computer executable code programmed by one skilled in the art to perform the method and workflow steps or functions of FIG. 1. Accordingly, by executing the computer program instructions, the processor 1104 executes the method and workflow steps or functions of FIG. 1. Computer 1102 may also include one or more network interfaces 1106 for communicating with other devices via a network. Computer 1102 may also include one or more input/output devices 1108 that enable user interaction with computer 1102 (e.g., display, keyboard, mouse, speakers, buttons, etc.).

Processor 1104 may include both general and special purpose microprocessors, and may be the sole processor or one of multiple processors of computer 1102. Processor 1104 may include one or more central processing units (CPUs), for example. Processor 1104, data storage device 1112, and/or memory 1110 may include, be supplemented by, or incorporated in, one or more application-specific integrated circuits (ASICs) and/or one or more field programmable gate arrays (FPGAs).

Data storage device 1112 and memory 1110 each include a tangible non-transitory computer readable storage medium. Data storage device 1112, and memory 1110, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1108 may include peripherals, such as a printer, scanner, display screen, etc. For example, input/output devices 1108 may include a display device such as a cathode ray tube (CRT) or liquid crystal display (LCD) monitor for displaying information to the user, a keyboard, and a pointing device such as a mouse or a trackball by which the user can provide input to computer 1102.

An image acquisition device 1114 can be connected to the computer 1102 to input image data (e.g., medical images) to the computer 1102. It is possible to implement the image acquisition device 1114 and the computer 1102 as one device. It is also possible that the image acquisition device 1114 and the computer 1102 communicate wirelessly through a network. In a possible embodiment, the computer 1102 can be located remotely with respect to the image acquisition device 1114.

Any or all of the systems and apparatus discussed herein may be implemented using one or more computers such as computer 1102.

One skilled in the art will recognize that an implementation of an actual computer or computer system may have other structures and may contain other components as well, and that FIG. 11 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
   receiving one or more input medical images of a vessel of a patient;
   performing a plurality of vessel assessment tasks for assessing the vessel using a machine learning based model trained using multi-task learning, the plurality of vessel assessment tasks performed by the machine learning based model based on shared features extracted from the one or more input medical images, the plurality of vessel assessment tasks comprising at least one of 1) classification of artifacts in the one or more input medical images as one of imaging artifacts and image processing artifacts or 2) classification of anomalies in the one or more input medical images as one of myocardial bridging and anomalies from prior interventions; and
   outputting results of the plurality of vessel assessment tasks or a combination of the results of the plurality of vessel assessment tasks.

2. The method of claim 1, wherein the plurality of vessel assessment tasks further comprises image-based stenosis grading of a stenosis in the vessel and wherein the image-based stenosis grading of the stenosis in the vessel is performed without using segmentation results of lumen of the vessel.

3. The method of claim 1, wherein the plurality of vessel assessment tasks further comprises image-based stenosis grading of a stenosis in the vessel and lumen segmentation from the one or more input medical images, and wherein results of the image-based stenosis grading and results of the lumen segmentation are consistent.

4. The method of claim 1, wherein the plurality of vessel assessment tasks further comprises a determination of one or more hemodynamic indices and lumen segmentation from the one or more input medical images, and wherein results of the determination of the one or more hemodynamic indices and results of the lumen segmentation are consistent.

5. The method of claim 1, wherein the plurality of vessel assessment tasks further comprises at least one of detection and classification of disease in the vessel, detection and classification of artifacts in the one or more input medical images, detection and classification of anomalies in the one or more input medical images, image-based stenosis grading of a stenosis in the vessel, and lumen segmentation from the one or more input medical images.

6. The method of claim 5, wherein the detection and classification of the disease in the vessel comprises classification of the disease as one of calcified, noncalcified, mixed calcified and noncalcified, and high risk.

7. The method of claim 1, wherein the machine learning based model is trained using unannotated clinical reports.

8. The method of claim 1, wherein outputting results of the plurality of vessel assessment tasks or a combination of the results of the plurality of vessel assessment tasks comprises:
outputting a heatmap for each of the plurality of vessel assessment tasks.

9. The method of claim 1, wherein performing a plurality of vessel assessment tasks for assessing the vessel using a machine learning based model trained using multi-task learning comprises:
determining a confidence measure for the results of the plurality of vessel assessment tasks.

10. The method of claim 1, wherein performing a plurality of vessel assessment tasks for assessing the vessel using a machine learning based model trained using multi-task learning comprises:
determining a confidence measure for each of the results of the plurality of vessel assessment tasks.

11. An apparatus comprising:
means for receiving one or more input medical images of a vessel of a patient;
means for performing a plurality of vessel assessment tasks for assessing the vessel using a machine learning based model trained using multi-task learning, the plurality of vessel assessment tasks performed by the machine learning based model based on shared features extracted from the one or more input medical images, the plurality of vessel assessment tasks comprising at least one of 1) classification of artifacts in the one or more input medical images as one of imaging artifacts and image processing artifacts or 2) classification of anomalies in the one or more input medical images as one of myocardial bridging and anomalies from prior interventions; and
means for outputting results of the plurality of vessel assessment tasks or a combination of the results of the plurality of vessel assessment tasks.

12. The apparatus of claim 11, wherein the plurality of vessel assessment tasks further comprises image-based stenosis grading of a stenosis in the vessel and wherein the image-based stenosis grading of the stenosis in the vessel is performed without using segmentation results of lumen of the vessel.

13. The apparatus of claim 11, wherein the plurality of vessel assessment tasks further comprises image-based stenosis grading of a stenosis in the vessel and lumen segmentation from the one or more input medical images, and wherein results of the image-based stenosis grading and results of the lumen segmentation are consistent.

14. The apparatus of claim 11, wherein the plurality of vessel assessment tasks further comprises a determination of one or more hemodynamic indices and lumen segmentation from the one or more input medical images, and wherein results of the determination of the one or more hemodynamic indices and results of the lumen segmentation are consistent.

15. A non-transitory computer readable medium storing computer program instructions, the computer program instructions when executed by a processor cause the processor to perform operations comprising:
receiving one or more input medical images of a vessel of a patient;
performing a plurality of vessel assessment tasks for assessing the vessel using a machine learning based model trained using multi-task learning, the plurality of vessel assessment tasks performed by the machine learning based model based on shared features extracted from the one or more input medical images, the plurality of vessel assessment tasks comprising at least one of 1) classification of artifacts in the one or more input medical images as one of imaging artifacts and image processing artifacts or 2) classification of anomalies in the one or more input medical images as one of myocardial bridging and anomalies from prior interventions; and
outputting results of the plurality of vessel assessment tasks or a combination of the results of the plurality of vessel assessment tasks.

16. The non-transitory computer readable medium of claim 15, wherein the plurality of vessel assessment tasks further comprises at least one of detection and classification of disease in the vessel, detection and classification of artifacts in the one or more input medical images, detection and classification of anomalies in the one or more input medical images, image-based stenosis grading of a stenosis in the vessel, and lumen segmentation from the one or more input medical images.

17. The non-transitory computer readable medium of claim 16, wherein the detection and classification of the disease in the vessel comprises classification of the disease as one of calcified, noncalcified, mixed calcified and noncalcified, and high risk.

* * * * *